United States Patent
Singh et al.

(10) Patent No.: US 12,318,280 B2
(45) Date of Patent: *Jun. 3, 2025

(54) REMOVABLE CAP ACTUATION FOR AN INTRAOCULAR LENS CARTRIDGE

(71) Applicant: Alcon Inc., Fribourg (CH)

(72) Inventors: Sudarshan B. Singh, Euless, TX (US); Todd Taber, Keller, TX (US); Yinghui Wu, Cedar Hill, TX (US); Douglas Brent Wensrich, Bedford, TX (US); Sam Jang, Woodbury, MN (US); Chris Pinkham, St. Paul, MN (US)

(73) Assignee: Alcon Inc., Fribourg (CH)

( * ) Notice: Subject to any disclaimer, the term of this patent is extended or adjusted under 35 U.S.C. 154(b) by 54 days.

This patent is subject to a terminal disclaimer.

(21) Appl. No.: 18/295,574

(22) Filed: Apr. 4, 2023

(65) Prior Publication Data

US 2023/0240837 A1  Aug. 3, 2023

Related U.S. Application Data

(63) Continuation of application No. 16/999,458, filed on Aug. 21, 2020, now Pat. No. 11,642,219.

(60) Provisional application No. 63/048,333, filed on Jul. 6, 2020, provisional application No. 62/890,859, filed on Aug. 23, 2019.

(51) Int. Cl.
*A61F 2/16* (2006.01)
(52) U.S. Cl.
CPC .......... *A61F 2/1678* (2013.01); *A61F 2/1667* (2013.01)

(58) Field of Classification Search
CPC ...... A61F 2/1662; A61F 2/1667; A61F 2/167; A61F 2/1672; A61F 2/1678; A61F 2/1691
See application file for complete search history.

(56) References Cited

U.S. PATENT DOCUMENTS

| | | | |
|---|---|---|---|
| 9,549,813 B2 * | 1/2017 | Anderson | A61F 2/167 |
| 11,793,921 B2 | 10/2023 | Köppel et al. | |
| 2010/0106160 A1 * | 4/2010 | Tsai | A61F 2/167 606/107 |
| 2012/0004772 A1 | 1/2012 | Rahilly et al. | |
| 2013/0041382 A1 * | 2/2013 | Ben Nun | A61F 2/1678 606/107 |
| 2016/0074155 A1 * | 3/2016 | Raquin | A61F 2/1672 606/107 |
| 2019/0105151 A1 * | 4/2019 | Tseng | A61F 2/1691 |
| 2019/0254812 A1 | 8/2019 | Maroschek | |

FOREIGN PATENT DOCUMENTS

| | | |
|---|---|---|
| JP | H10309294 A | 11/1998 |
| WO | 2013011024 A1 | 1/2013 |

* cited by examiner

*Primary Examiner* — Sarah W Aleman
(74) *Attorney, Agent, or Firm* — PATTERSON + SHERIDAN, LLP

(57) ABSTRACT

Systems, methods, and apparatuses for removably attaching a drive mechanism handpiece to an intraocular lens (IOL) cartridge that folds the IOL upon removal of a cap, are provided. The IOL cartridge comprises a nozzle and a housing comprising a slide. A compartment configured to receive an IOL is disposed within the housing. An interior portion of the slide is exposed to the compartment. The nozzle is in fluid communication with the compartment. The cap covers the nozzle and the slide. The cap is configured to expose the nozzle and advance the slide to fold the IOL upon removal of the cap.

20 Claims, 9 Drawing Sheets

REMOVABLE CAP ACTUATION FOR AN INTRAOCULAR LENS CARTRIDGE

CROSS-REFERENCE TO RELATED APPLICATIONS

This application is a continuation of U.S. Non-Provisional Patent Application No. 16/999,458, filed Aug.21, 2020, which claims benefit of and priority to U.S. Provisional Patent Application No. 62/890,859, filed Aug. 23, 2019, and U.S. Provisional Patent Application No. 63/048,333, filed Jul. 6, 2020, the contents of each of which are incorporated herein by reference in their entirety.

TECHNICAL FIELD

The present disclosure generally relates to eye surgery and, more particularly, some embodiments may generally relate to systems, methods, and apparatuses for removably attaching a drive mechanism handpiece to an intraocular lens (IOL) cartridge that folds the IOL upon removal of a cap.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery.

For cataract surgery, a surgical procedure may require incisions and insertion of tools within an eye to replace the clouded lens with an IOL. An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate compartment may be loaded into the insertion tool. The plunger may engage the IOL to advance the IOL from the compartment, through a nozzle, and into the eye.

SUMMARY

In an exemplary embodiment, the present disclosure provides an intraocular lens (IOL) cartridge that manipulates the IOL upon removal of a cap. The IOL cartridge comprises a housing, a nozzle coupled to the housing, and an actuator coupled to the housing. The housing may include a compartment configured to receive an IOL, and the nozzle may be in fluid communication with the compartment. The actuator may be configured to slide along an exterior portion of the housing relative to the compartment from a first position to a second position to actuate a mechanism to manipulate the IOL for delivery. The IOL cartridge may further include a cap, which may at least partially cover the nozzle, the housing, and the actuator. The cap may be configured to advance the actuator from the first position to the second position and to expose the nozzle as the cap is removed from the IOL cartridge.

In another exemplary embodiment, the present disclosure provides an IOL cartridge that folds the IOL upon removal of a cap. The IOL cartridge comprises the cap, a nozzle and a housing comprising a slide. The slide comprises two sets of internal ramps. A compartment configured to receive an IOL is disposed within the housing. An interior portion of the slide is exposed to the compartment. The nozzle is in fluid communication with the compartment. The cap covers the nozzle and the slide. The cap is configured to expose the nozzle and advance the slide to move the internal ramps to fold the IOL upon removal of the cap. The IOL cartridge may also include a plunger case that is in fluid communication with the compartment, wherein a plunger is movably disposed within the plunger case.

In another exemplary embodiment, the present disclosure provides a method for delivery of an IOL into an eye. The method comprises attaching an IOL cartridge to a handpiece. The IOL cartridge comprises a cap, a nozzle, and a housing comprising a slide. The cap covers the nozzle and the slide. A compartment comprising an IOL is disposed within the housing. An interior portion of the slide is exposed to the compartment. The nozzle is in fluid communication with the compartment. The IOL cartridge may also include a plunger case that is in fluid communication with the compartment, wherein a plunger is movably disposed within the plunger case. The method further includes removing the cap to expose the nozzle and advance the slide to fold the IOL.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
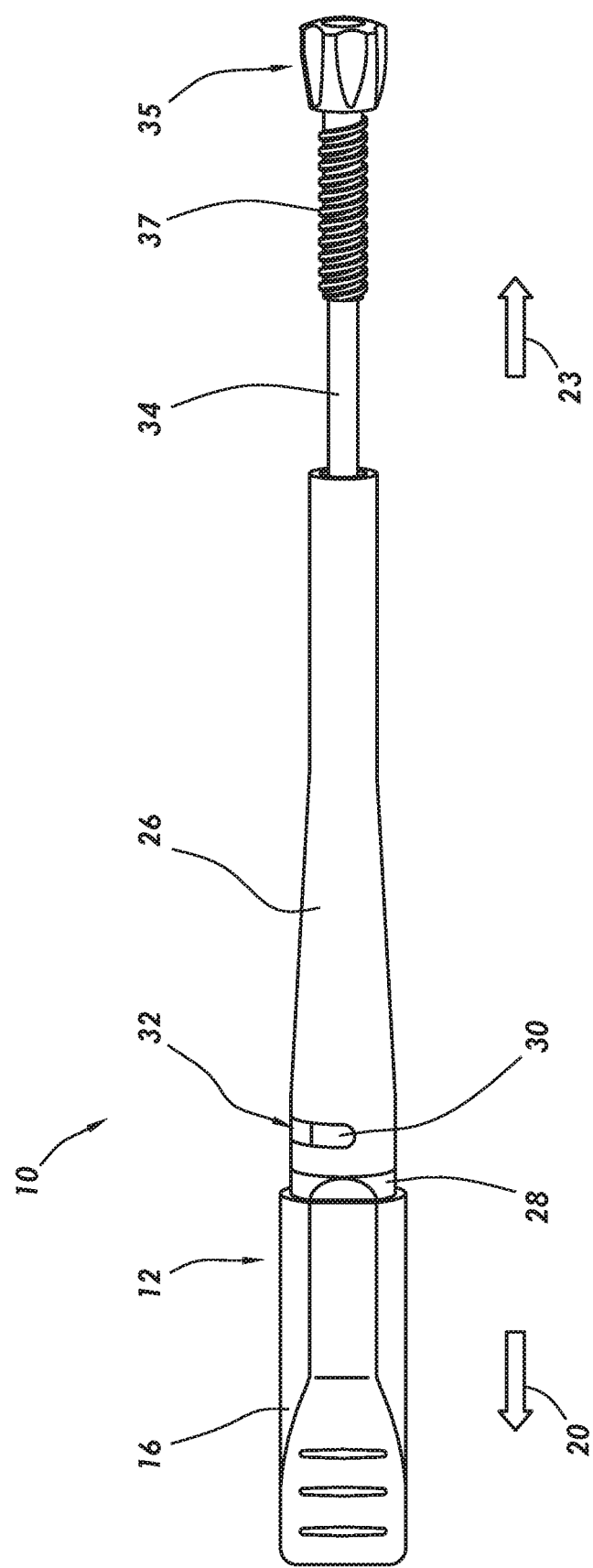
FIG. 1 illustrates a top perspective view of an insertion tool including an IOL cartridge with a removable cap, in accordance with some embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments of the present disclosure provide an intraocular lens cartridge ("IOL cartridge") that folds the IOL upon removal of a cap. The cap may initially cover a nozzle of the IOL cartridge to protect the nozzle from any damage during storage and/or shipping. Removing the cap exposes the nozzle and also actuates a folding mechanism of the IOL cartridge to fold the IOL for delivery into an eye. The IOL cartridge may be a preloaded cartridge that is preloaded with the IOL. The IOL cartridge may be part of a modular delivery system that includes a universal interface for removable attachment to various handpieces that include different types of drive mechanisms.

Particular embodiments of the present disclosure allow interchangeability between different handpieces such as disposable and reusable handpieces, and the IOL cartridge. The disposable handpieces may include manual drive mechanisms (e.g., manually actuated via pushing or screwing, and/or manually actuated via a fluid or a resilient member such as a spring) that are not electrically powered. The reusable handpieces may include the manual drive mechanisms as well as electrically powered drive mechanisms (e.g., stator windings). It should be noted that these types of handpieces are examples and that other types of handpieces or drive mechanisms may be utilized in accordance with particular embodiments of the present disclosure.

Particular embodiments of the present disclosure allow assembling of the handpiece to the IOL cartridge, delivering the IOL, and disengaging the handpiece from the used IOL cartridge, if needed. The universal interface allows the different types of handpieces to be easily paired to and utilized with the IOL cartridge for IOL implantation. A handpiece may be secured to the IOL cartridge by sliding an end of the handpiece over the plunger case of the IOL cartridge to form an insertion tool. Once the insertion tool is formed, the IOL may be delivered into an eye. After the IOL implantation, the IOL cartridge can be easily detached from the handpiece (e.g., a reusable handpiece) by pulling the handpiece from the IOL cartridge.

FIG. 1 illustrates a top perspective view of an insertion tool 10 including an IOL cartridge 12, in accordance with some embodiments of the present disclosure. A removable cap ("cap") 16 may cover the IOL cartridge 12. The cap 16 may be removed (e.g., pulled or pushed in a direction indicated by a directional arrow 20) from the IOL cartridge 12 to expose a nozzle (not shown) of the IOL cartridge 12. Additionally, removal of the cap 16 rotates internal components of the IOL cartridge 12 to manipulate an IOL, such as by folding and/or compressing the IOL (not shown) for delivery into an eye.

The insertion tool 10 may include a handpiece 26 removably attached to the IOL cartridge 12. It should be noted that various handpieces may be used with different types of IOL cartridges. The handpiece 26 may include an electrically powered or a non-electrically powered drive mechanism that may include a push rod 34 extending along a length of the handpiece 26. The push rod 34 may be movably disposed within the handpiece 26 and may be manually actuated via a rotatable knob 35, which may cooperate with a fluid or a resilient member such as a spring 37 or another actuation mechanism. The push rod 34, upon actuation, may advance a plunger (not shown) that may be movably disposed within the plunger case 28. In general, for the purposes of discussing and describing the various components and features of the handpiece 26 and the IOL cartridge 12, reference to a proximal end or direction may refer to a direction more towards an end of the handpiece 26 comprising the rotatable knob 35, according to a directional arrow 23. Likewise, reference to a distal end or direction may refer to a direction more towards an end of the IOL cartridge 12 comprising the cap 16, according to the directional arrow 20.

The IOL cartridge 12 may include a plunger case 28. The plunger case 28 may be a rigid, hollow, and tubular member that may be inserted into the handpiece 26 and secured therein via a projection 30 that extends from the plunger case 28. The projection 30 is mated (e.g., via rotation) to the handpiece 26 via a slot 32 of the handpiece 26.

Figure 2:
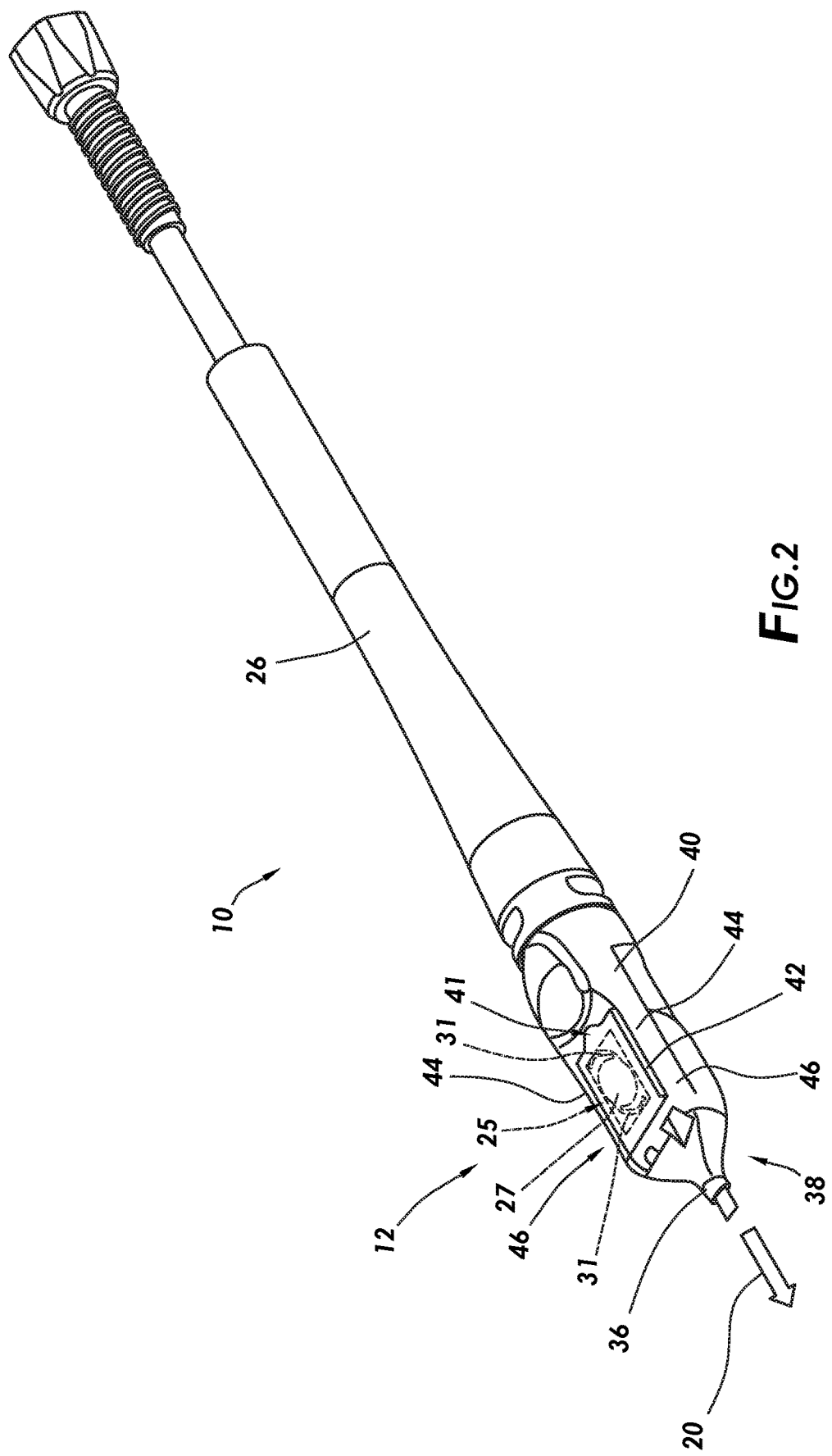
FIG. 2 illustrates the insertion tool of FIG. 1 without the cap shown, in order to illustrate components beneath the cap that are configured in an initial non-actuated position, in accordance with some embodiments of the present disclosure.

FIG. 2 illustrates the insertion tool 10 of FIG. 1 without the cap 16 shown in order to illustrate components beneath the cap 16 that are configured in an initial non-actuated position, in accordance with some embodiments of the present disclosure. The IOL cartridge 12 includes a nozzle 36 that is positioned at a distal end 38 of a housing 40 of the IOL cartridge 12. The housing 40 may include a compartment 41 which may be in fluid communication with the nozzle 36. The compartment 41 may contain an IOL 25. The IOL 25 may be any suitable intraocular lens. The IOL 25 may include a lens portion 27 and haptic extensions 31. The haptic extensions 31 may be side struts (or other suitable extensions) extending from the lens portions 27 that may stabilize the IOL 25 when it may be disposed within the patient's eye. It should be understood that the IOL 25 is merely exemplary and that techniques disclosed herein may be used with any suitable IOL. For example, a modular IOL (not shown) that includes a lens portion disposable in a base with haptic extensions can also be used.

The housing 40 may include a movable or slidable actuator, such as slide 42, that is movably disposed within tracks 44 of the housing 40. The tracks 44 may be integrated into lateral portions 46 of the housing 40. The cap 16 (e.g., shown on FIG. 1) may cover the housing 40 and the nozzle 36. An interior portion (not shown) of the cap 16 may contact the slide 42 and move the slide 42 in a direction indicated by the directional arrow 20, as the cap 16 is removed. For example, the slide 42 may be moved from an initial first position to a second position. In the illustrated embodiment, the slide 42 is in an initial non-advanced position, or first position. In this initial position, the cap 16 has not been removed and the IOL 25 is in an unfolded and uncompressed state.

Figure 3:
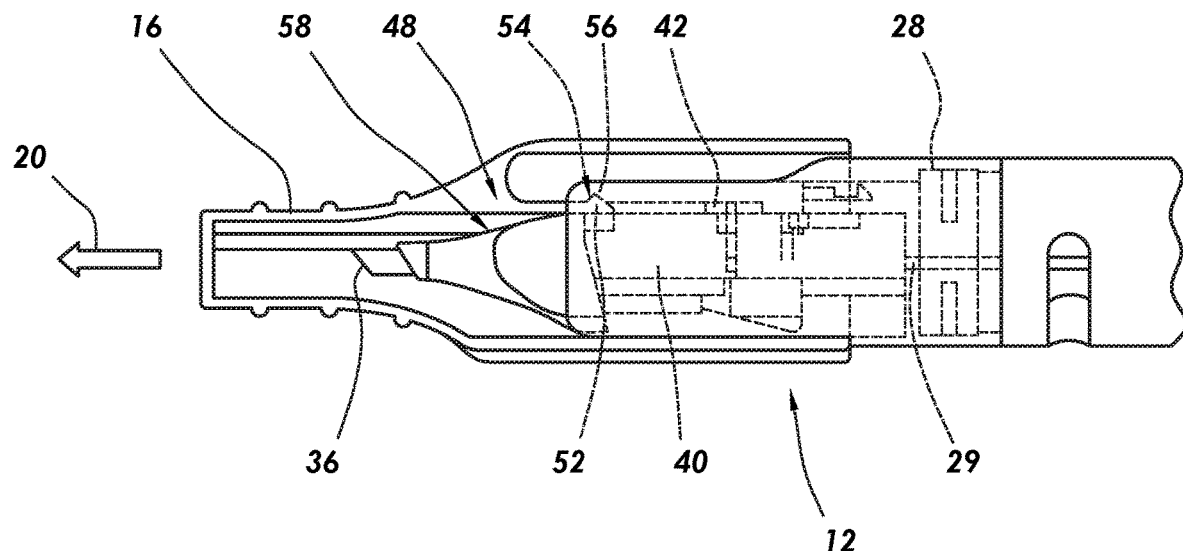
FIG. 3 illustrates a cutaway side view of the cap at least partially covering the IOL cartridge with a slide of the IOL cartridge in an initial non-advanced position, in accordance with some embodiments of the present disclosure.

FIG. 3 illustrates a cutaway side view of the cap 16 at least partially covering the IOL cartridge 12 with the slide 42 in the initial non-advanced position, in accordance with some embodiments of the present disclosure. In the illustrated embodiment, an interior portion 48 (e.g., an interior top portion) of the cap 16 may include a latch 52 that extends (e.g., upward) into a notch 54 positioned on an underside of an extension 56 of the slide 42 to removably fasten the cap 16 to the slide 42. As the cap 16 is pulled in a direction indicated by the directional arrow 20, the cap 16 moves the slide 42 forward in the direction 24. Moving the cap 16 causes the latch 52 of the cap 16 to disengage from the notch 54 of the slide 42 due to the latch 52 dropping, in elevation, along a tapered portion 58 of the nozzle 36, thereby releasing the cap 16 from the IOL cartridge 12. As previously noted, the cap 16 covers the nozzle 36 and the housing 40 (including the slide 42) of the IOL cartridge 12. The plunger 29 may be movably disposed within the plunger case 28. The plunger 29 may extend lengthwise within the plunger case 28. It should be noted only a portion of the plunger 29 is shown.

Figure 4:
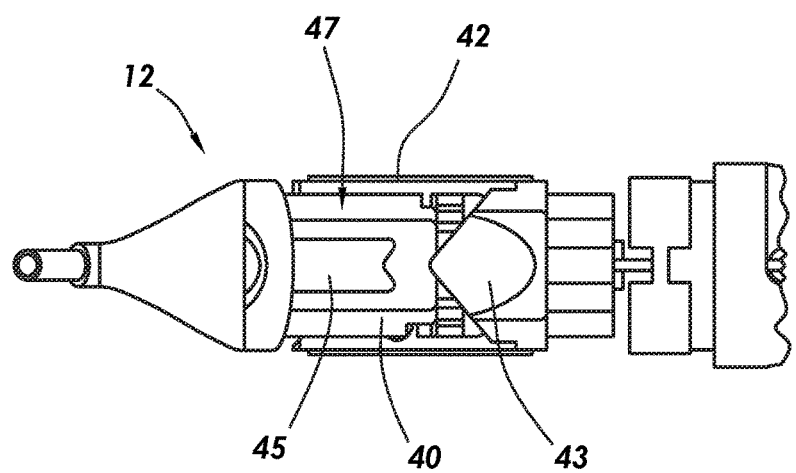
FIG. 4 illustrates a bottom view of the slide of the IOL cartridge of FIG. 3 in the initial non-advanced position, in accordance with some embodiments of the present disclosure.

FIG. 4 illustrates a bottom view of the slide 42 of the IOL cartridge 12 of FIG. 3 in the initial non-advanced position (i.e., the cap 16 is not removed from the IOL cartridge 12 and the IOL 25 is in an unfolded state), in accordance with some embodiments of the present disclosure. In the illustrated embodiment, at least a portion (e.g., a bottom portion 43 of the slide 42) of the slide 42 may completely circumferentially encompass the housing 40. The bottom portion 43 may be configured to contact a slide stop 45 of the housing 40. The slide stop 45 may extend outward from a bottom exterior portion 47 of the housing 40. The slide stop 45 may prevent the slide 42 from sliding off or separating from the housing 40 of the IOL cartridge 12, as the slide 42 moves forward upon removal of the cap 16.

Figure 5:
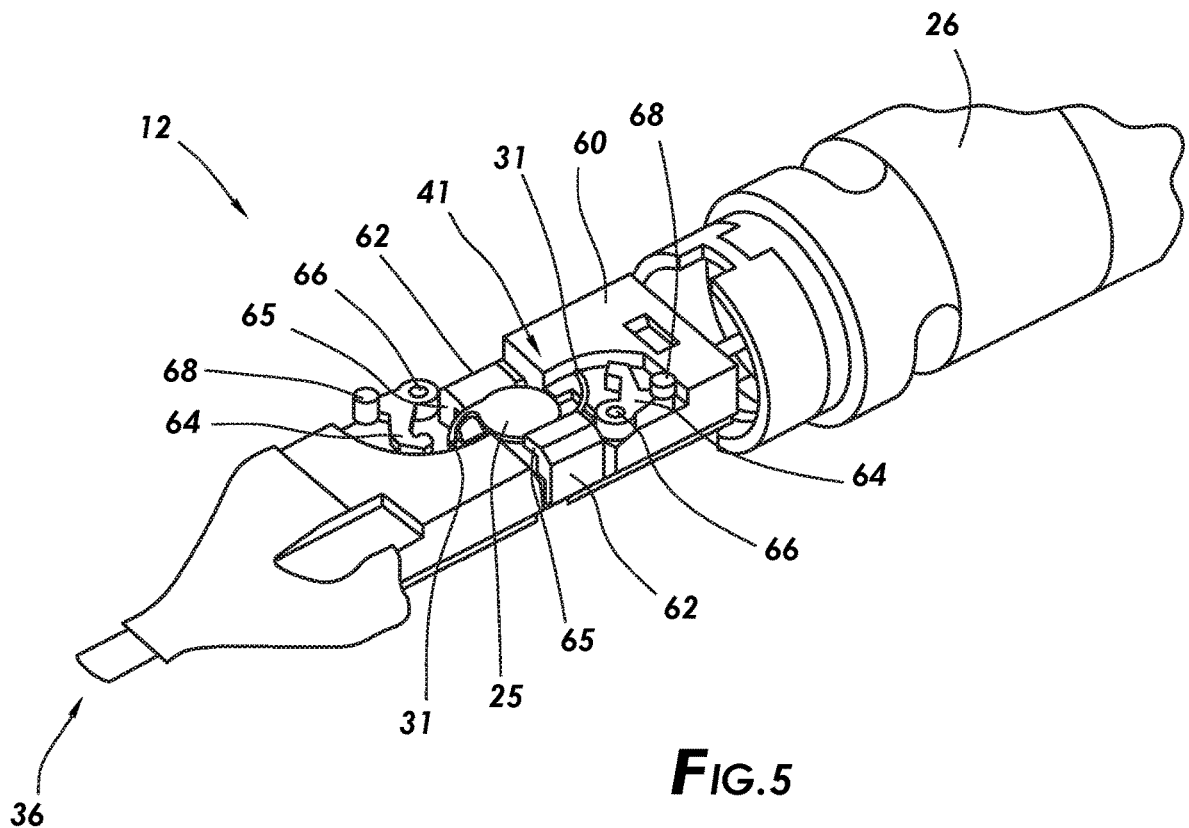
FIG. 5 illustrates a cutaway top perspective view of the IOL cartridge without depicting the cap and the slide in order to show components beneath the slide that are in an initial non-actuated configuration, in accordance with particular embodiments of the present disclosure.

FIG. 5 is a cutaway top perspective view of the IOL cartridge 12 without depicting the cap 16 (e.g., shown on FIG. 1) and the slide 42 (e.g., shown on FIG. 2) in order to show components beneath the slide 42 that are in an initial non-actuated configuration, in accordance with particular embodiments of the present disclosure. As shown, the IOL cartridge 12 is coupled to the handpiece 26. An interior portion 60 of the housing 40 of the IOL cartridge 12 may include the compartment 41. The compartment 41 may include one or more mechanisms, which may include one or more sets of IOL manipulators, for engaging with the IOL 25 in order to fold, splay, straighten, or otherwise manipulate the IOL 25. For example, a folding mechanism may include edge rollers 62 pivotably attached to the interior portion 60. Pins (not shown) may extend laterally from the edge rollers 62 into the interior portion 60 of the housing 40, thereby enabling rotation (e.g., in a vertical direction) of the edge rollers 62. The interior portion 60 may also include compression arms 64 that are also pivotably disposed within the interior portion 60 via pins 66 which extend vertically through the compression arms 64 into the interior portion 60 to allow rotation (e.g., in a lateral direction) of the compression arms 44. The compression arms 64 may include projections 68 that may extend upward to contact internal ramps (not shown) of the slide 42. The IOL 25 may be disposed at a center of the interior portion 60, within the compartment 41, and between the compression arms 64 and the edge rollers 62. The IOL 25 may be preloaded and held in place within grooves 65 of the edge rollers 62. The edge rollers 62, upon actuation (i.e., removal of the cap 16), rotate inward and downward (e.g., vertical rotation) to fold the IOL 25. Simultaneously, upon actuation, the compression arms 64 laterally rotate inward to compress the haptic extensions 31. Once compressed and folded, the IOL 25 is ready for delivery through the nozzle 36.

Figure 6:
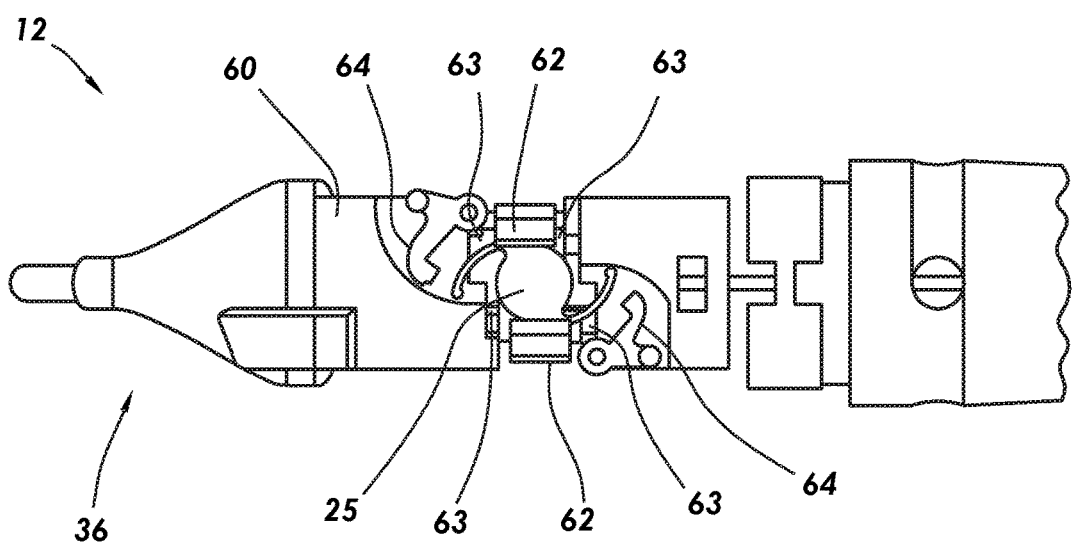
FIG. 6 illustrates a top view of the IOL cartridge of FIG. 5, in accordance with particular embodiments of the present disclosure.

FIG. 6 is a top view of the IOL cartridge 12 of FIG. 5, in accordance with particular embodiments of the present disclosure. Pins 63 extend from the edge rollers 62 into the interior portion 60, thereby enabling rotation of the edge rollers 62, upon removal of the cap 16 (e.g., shown on FIG. 1). Removal of the cap 16 causes rotation of the edge rollers 62 and the compression arms 64 thereby folding and compressing the IOL 25 for delivery through the nozzle 36.

Figure 7:
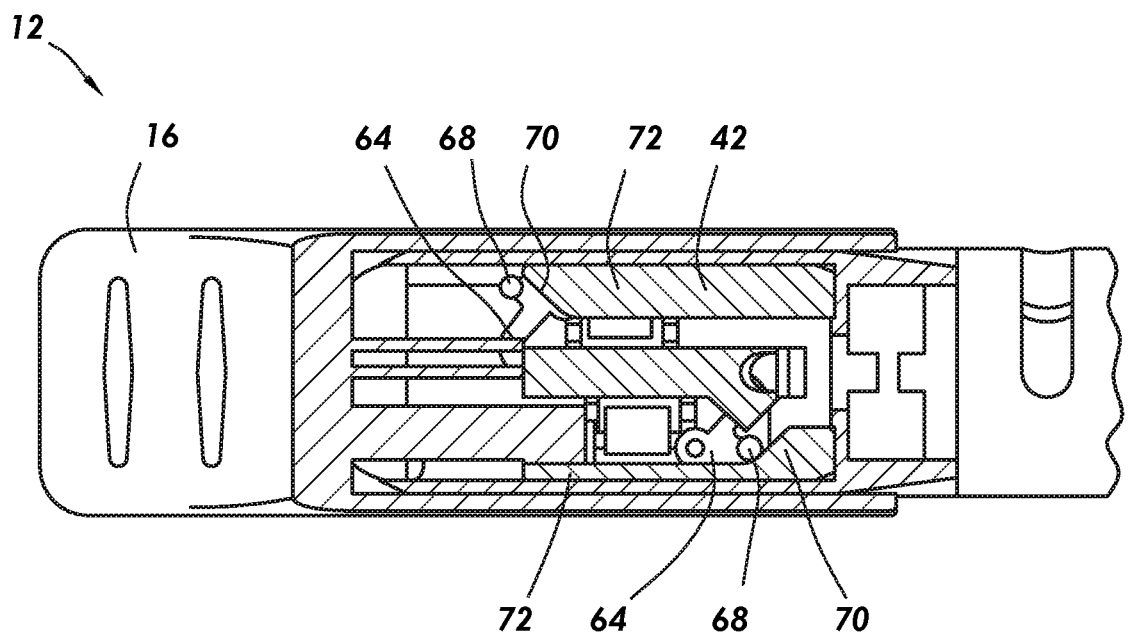
FIG. 7 illustrates a cutaway top view of the IOL cartridge with the cap disposed over the IOL cartridge, in accordance with particular embodiments of the present disclosure.

FIG. 7 illustrates a cutaway top view of the IOL cartridge 12 with the cap 16 disposed over the IOL cartridge 12, in accordance with particular embodiments of the present disclosure. The cap 16 provides protective coverage for the IOL cartridge 12 and maintains the IOL 25 (e.g., shown on FIG. 5) in a non-folded state during storing and/or shipping of the IOL cartridge 12. The slide 42 may include internal ramps 70 that are aligned with the projections 68 of the compression arms 64. The internal ramps 70 may extend inward from lateral portions 72 of the slide 42. The internal ramps 70 may be configured to guide the projections 68 along the internal ramps 70, as the cap 16 is removed. The compression arms 64 may rotate inward (e.g., lateral rotation) as the cap 16 is removed and the projections 68 move along the internal ramps 70 thereby compressing the haptic extensions 31 (e.g., shown on FIG. 5).

Figure 8:
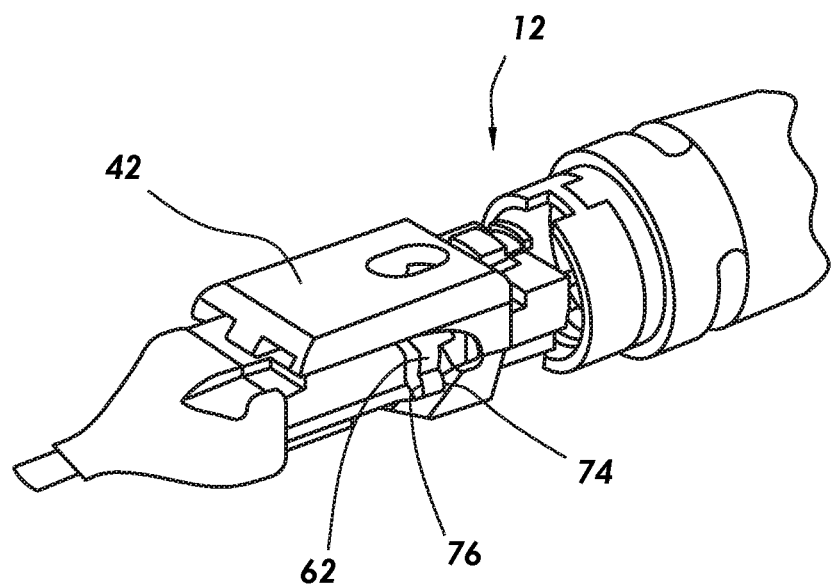
FIG. 8 illustrates a cutaway side perspective view of the IOL cartridge with the slide in the initial non-advanced position, in accordance with particular embodiments of the present disclosure.

FIG. 8 illustrates a cutaway side perspective view of the IOL cartridge 12 with the slide 42 in the initial non-advanced position, in accordance with particular embodiments of the present disclosure. The cap 16 is not shown to illustrate the initial non-advanced position of the slide 42 before actuation of the edge rollers 62 and the compression arms 64, as shown on FIGS. 5 and 6. Although not illustrated, an opposite side of the IOL cartridge 12 is configured similarly to the side that is depicted. The slide 42 may include an internal ramp 74 that is aligned with a lower portion 76 of the edge roller 62. The internal ramp 74 may extend upward and may be configured to guide and receive the lower portion 76 of the edge roller 62, as the cap 16 is removed. As the lower portion 76 is contacted by the internal ramp 74, the edge roller 62 may rotate vertically to fold the IOL 25 (e.g., shown on FIG. 5). As the cap 16 is removed, the internal ramps 74 of the slide 42 may advance to contact the lower portions 76 of the edge rollers 62, which may cause the lower portions 76 of the edge rollers 62 to be lifted or raised. The raising or lifting of the lower portions 76 may cause the edge rollers 62 to rotate, resulting in other portions of the edge rollers 62 in contact with the IOL 25, such as the grooves 65, to push the IOL 25 downward, thereby folding the IOL 25.

Figure 9:
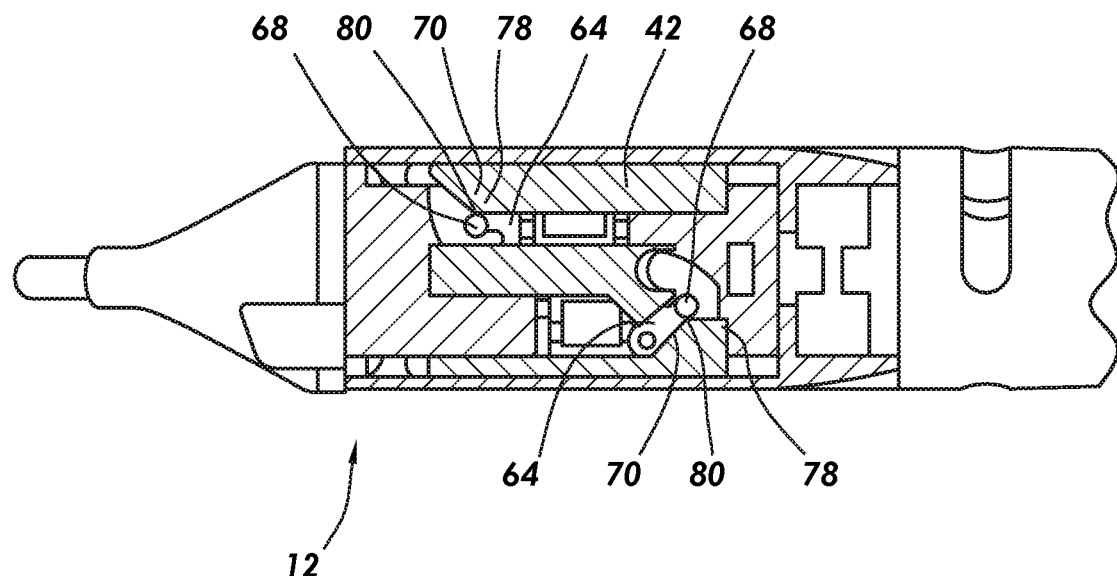
FIG. 9 illustrates a cutaway top view of the IOL cartridge with the cap removed and the slide in an advanced position, in accordance with particular embodiments of the present disclosure.

FIG. 9 illustrates a cutaway top view of the IOL cartridge 12 with the cap 16 removed and the slide 42 in the advanced position, in accordance with particular embodiments of the present disclosure. With the removal of the cap 16 (e.g., shown on FIG. 1), the internal ramps 70 of the slide 42 have been advanced and the projections 68 of the compression arms 64 have moved along the internal ramps 70 to flat portions 78 of the slide 42. The flat portions 78 are adjacent to apexes 80 of the internal ramps 70. In the illustrated configuration, the compression arms 64 are laterally rotated inward and the haptic extensions 31 (shown on FIGS. 5 and 6) are compressed.

Figure 10:
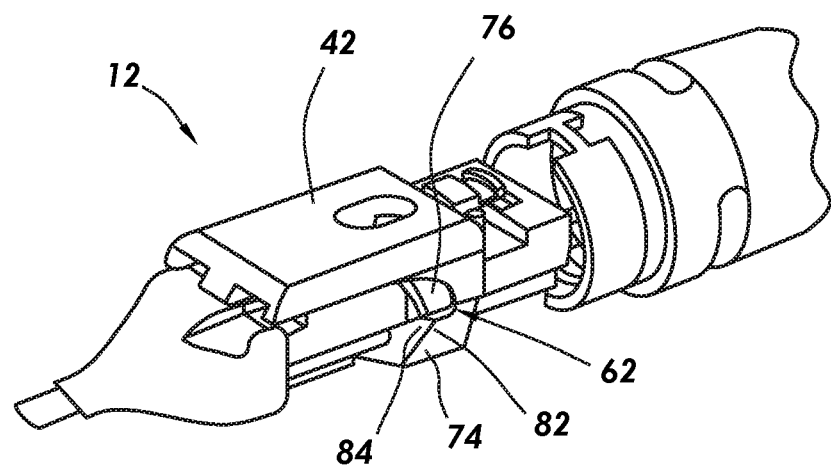
FIG. 10 illustrates a cutaway side perspective view of the IOL cartridge with the cap removed and the slide in the advanced position, in accordance with particular embodiments of the present disclosure.

FIG. 10 illustrates a cutaway side perspective view of the IOL cartridge 12 with the cap 16 removed and the slide 42 in the advanced position, in accordance with particular embodiments of the present disclosure. As previously noted, the opposite side of the slide 42 may be configured similarly to the side that is illustrated. In the illustrated embodiment, the slide 42 is in the advanced position and the IOL 25 is in a folded state (not shown). The internal ramp 74 has been advanced and the lower portion 76 of the edge roller 62 has been vertically rotated and is positioned on a flat portion 82 that may be adjacent to an apex 84 of the internal ramp 74. Upon advancement of the internal ramps 74 of the slide 42, the lower portions 76 of the edge rollers 62 are vertically rotated and positioned on the flat portions 82, and the IOL 25 is in a folded state.

Figure 11:
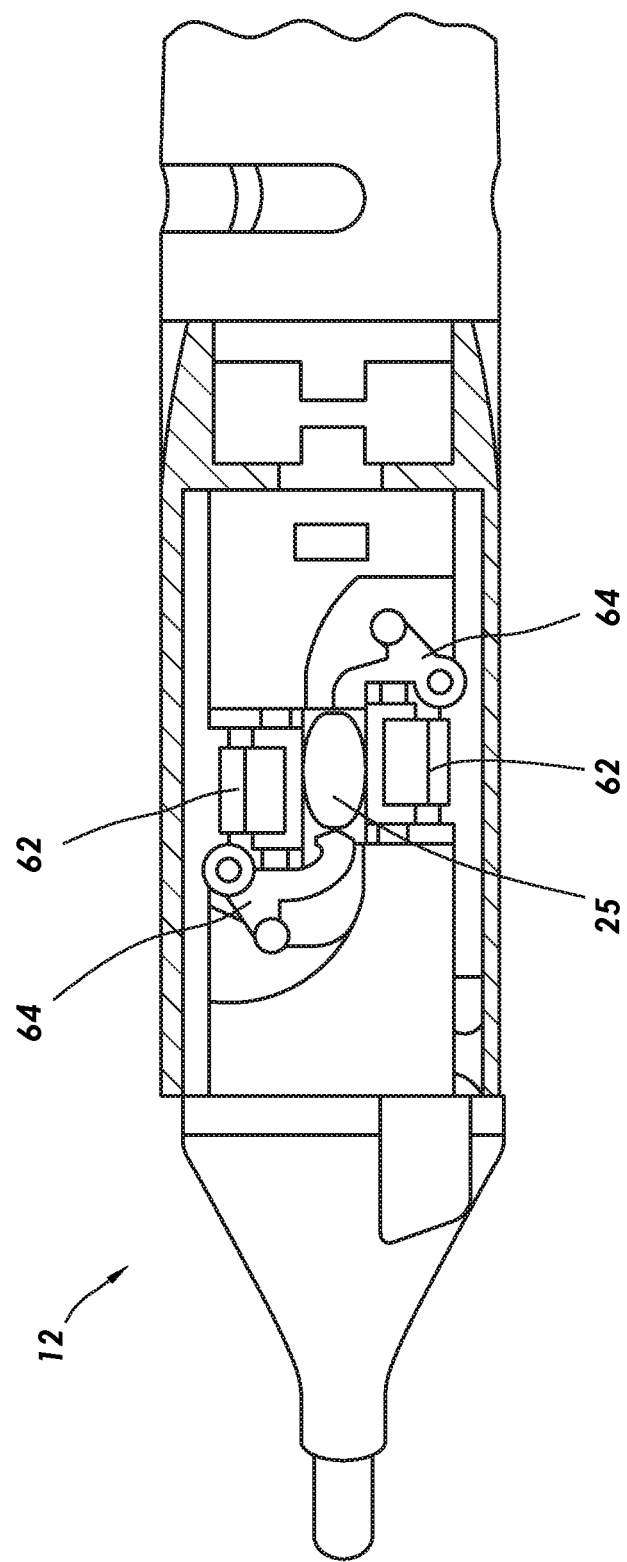
FIG. 11 illustrates a cutaway top view of the IOL cartridge with internal folding components in their actuated positions, in accordance with particular embodiments of the present disclosure.

FIG. 11 illustrates a cutaway top view of the IOL cartridge 12 with the edge rollers 62 and the compression arms 64 in their rotated positions, in accordance with particular embodiments of the present disclosure. The cap 16 has been removed to advance the slide 42 (e.g., shown on FIG. 10) thereby actuating the edge rollers 62 and the compression arms 64. In the illustrated embodiment, the slide 42 is not shown to allow viewing of the edge rollers 62 and the compression arms 64 in their rotated (actuated) positions. The edge rollers 62 have rotated vertically to fold the IOL 25, and the compression arms 64 have rotated laterally to compress the haptic extensions 31 (shown on FIGS. 5 and 6) of the IOL 25.

Figure 12:
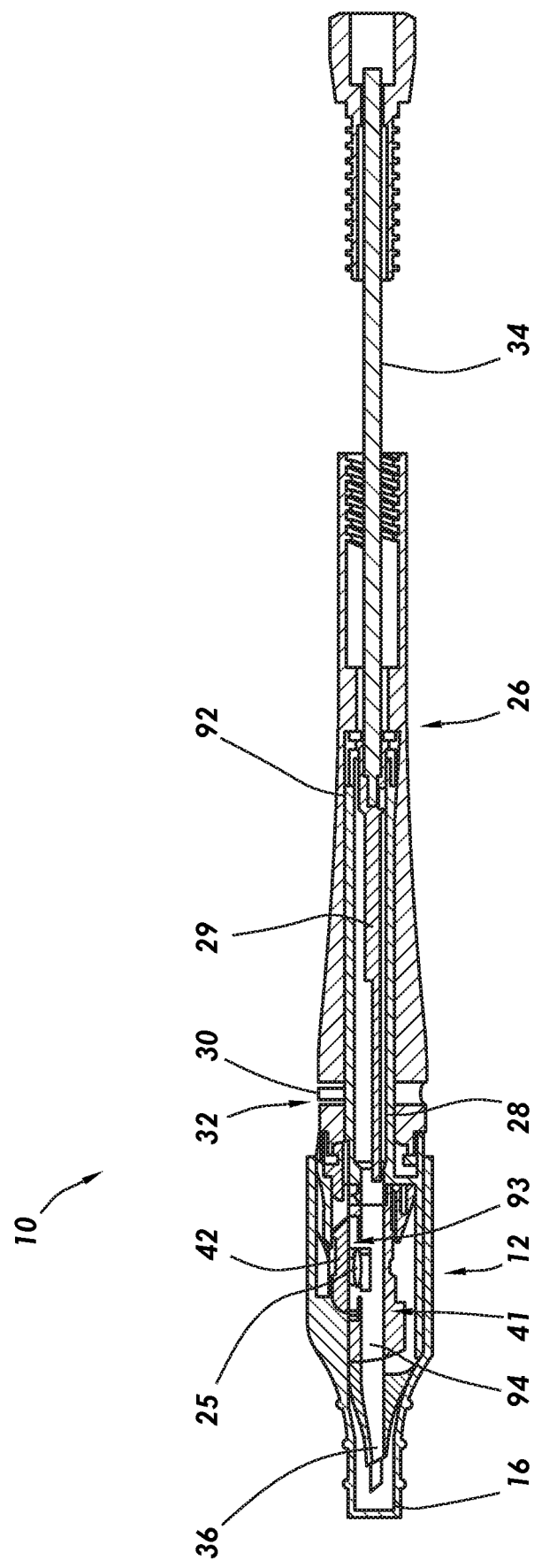
FIG. 12 illustrates a side cross-sectional view of an IOL cartridge removably attached to a handpiece.

FIG. 12 illustrates a side cross-sectional view of the insertion tool 10 in accordance with particular embodiments of the present disclosure. In the illustrated embodiment, the plunger case 28 may be disposed within a housing 92 of the handpiece 26 and secured therein via the projection 30. The plunger case 28 is in fluid communication with the compartment 41. An interior portion 93 of the slide 42 is exposed to the compartment 41. As previously noted, the plunger 29 may be movably disposed within the plunger case 28. After the cap 16 is removed thereby advancing the slide 42 forward, the push rod 34 of the handpiece 26 may be actuated to advance the plunger 29 forward to deliver the IOL 25, in the folded and compressed state, from the compartment 41 through a passage 94 and the nozzle 36, and into a patient's eye. The passage 94 may extend from the compartment 41 and through the nozzle 36. After delivery of the IOL 25, the nozzle 36 may be removed from the patient's eye. Then, the handpiece 26 may be rotated to release the projection 30 of the IOL cartridge 12 from the slot 32 of the handpiece 26. The handpiece 26 may then be pulled from the IOL cartridge 12 to disengage the IOL cartridge 12 from the handpiece 26. The used IOL cartridge 12 may then be disposed.

With reference to FIGS. 1-12, an exemplary technique for assembling the IOL cartridge 12 to the handpiece 26 to form the insertion tool 10, in accordance with particular embodiments of the present disclosure is described as follows.

First, the plunger case 28 of the IOL cartridge 12 with the cap 16 disposed thereon, may be inserted into the handpiece 26 to secure the IOL cartridge 12 to the handpiece 26 thereby forming the insertion tool 10, as shown on FIG. 1, for example. Then, the cap 16 may be removed to expose the nozzle 36. As the cap 16 is removed, the IOL 25 is manipulated to be in a folded and compressed configuration, as shown on FIG. 11, for example. As previously mentioned, in additional or alternative embodiments, in addition to or instead of folding the IOL 25, the cap 16, slide 42, and/or the housing 40 of the IOL cartridge 12 may be configured such that removal of the cap 16 causes one or more portions of the IOL 25, such as the haptic extensions 31, to be straightened or splayed. Upon actuation of the push rod 34, the plunger 29 may advance forward to deliver the IOL 25 from the compartment 41 through the nozzle 36. To disassemble the insertion tool 10 after delivery of the IOL 25, the IOL cartridge 12 may be rotated and pulled out from the handpiece 26 thereby sliding the plunger case 28 out from the handpiece 26 to form a separate IOL cartridge 12 and a separate handpiece 26.

Figure 13:
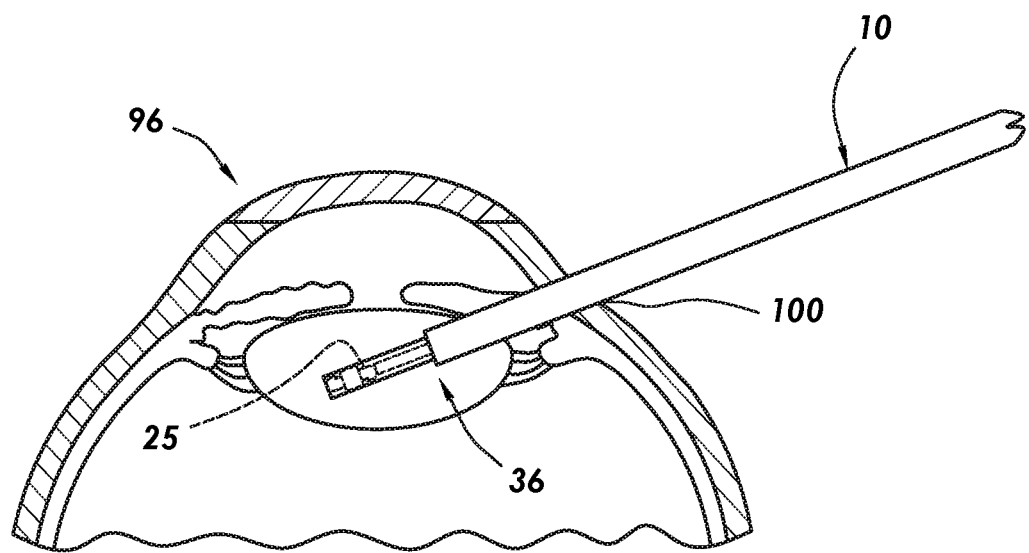
FIGS. 13 and 14 illustrate implantation of an IOL in accordance with some embodiments of the present disclosure.
Figure 14:
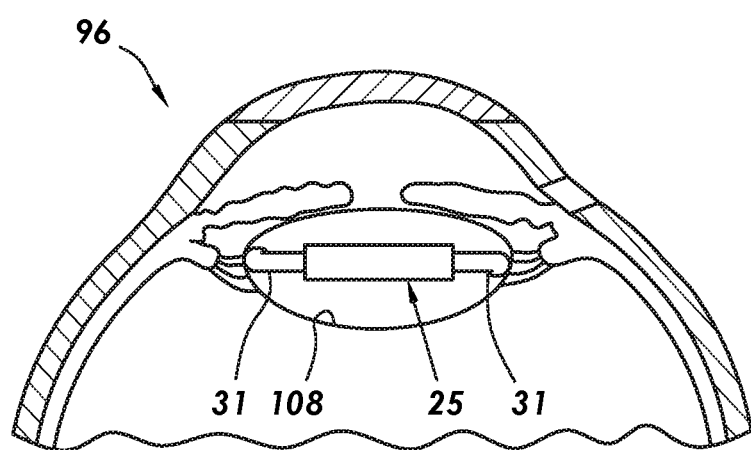

FIGS. 13 and 14 illustrate an exemplary technique for implantation of the IOL 25 into an eye 96 of a patient in accordance with particular embodiments of the present disclosure. FIG. 13 illustrates an incision 100 may be made in the eye 96 by a surgeon. For example, the incision 100 may be made through the sclera of the eye 96. The incision 100 may be a suitable width or length. Without limitation, the suitable width and/or length may be less than 3 millimeters, and in some instances may be less than 2 millimeters. After the incision 100 is made, the nozzle 36 of the insertion tool 10 may be inserted through the incision 100 into an interior portion of the eye 96. The insertion tool 10 may be actuated to dispense the IOL 25 into a capsular bag 108 of the eye 96, as shown on FIG. 14.

The IOL 25 may be delivered in a folded (or rolled configuration) and allowed to unfurl after ejection from the insertion tool 10. Upon dispensation, the IOL 25 should unfurl and settle within the capsular bag 108 of the eye 96, as shown on FIG. 14. The haptic extensions 31 may be manipulated, for example, to engage an equator of the capsular bag 108. The haptic extensions 31 may engage the capsular bag 108 to secure the IOL 25 in the capsular bag 108.

Use of the methods and systems described herein may provide numerous benefits and advantages over other IOL delivery systems. For example, folding or other manipulation of the IOL may be streamlined. The integrated functionality of the folding or other manipulation of the IOL 25 with the removal of the cap 16 of the IOL cartridge 12 may ensure that the IOL insertion tool 10 is used correctly and may guard against potential user errors. For example, in order to expose the nozzle 36 of the IOL cartridge, the cap 16 must first be removed, thus causing the IOL 25 to be folded and put into a proper configuration for delivery. This integrated functionality of the removable cap 16 may thus ensure that a proper sequence of steps for preparing, configuring, and delivering an IOL are followed, and therefore may guard against premature delivery or ejection of the IOL 25 prior to proper folding or other configuring.

Additionally, the interchangeable utilization between different drive mechanisms and the preloaded IOL cartridge offers a simplified and uniform process for pairing drive mechanisms to preloaded IOL cartridges. Thus, a variety of handpieces employing different types of drive mechanisms may be used with each of numerous different types of IOL cartridges, and therefore different types of IOLs. For example, a user may readily select between multiple types of drive mechanisms he or she wishes to use depending on the type of IOL and/or the type of IOL cartridge. Additionally, while one user may prefer to use a first type of drive mechanism handpiece for a given IOL cartridge, a different user may have the option of using a second type of drive mechanism handpiece for the same given type of IOL cartridge. Importantly, by allowing for a common, or standard interface for securing the handpieces to the IOL cartridges, the user experience of securing a handpiece to an IOL cartridge may be substantially the same, regardless of the type of drive mechanism or type of IOL cartridge, and thus IOL, being used, which may also increase ease-of-use for an operator as well as streamline IOL delivery procedures.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An intraocular lens (IOL) cartridge comprising:
   a housing comprising a compartment configured to receive an IOL;
   a nozzle coupled to the housing and in fluid communication with the compartment;
   an actuator coupled to the housing and configured to translate along an exterior portion of the housing relative to the compartment from a first position to a second position;
   a first and a second set of internal ramps operably connected to the actuator; and
   a cap adapted to at least partially cover at least one of the nozzle, the housing, or the actuator, the cap configured to translate the actuator from the first position to the second position as the cap is removed from the IOL cartridge,
   wherein as the actuator is translated from the first position to the second position, the first and the second set of internal ramps are configured to actuate a first and a second set of IOL manipulators, respectively, to manipulate the IOL for delivery.

2. The IOL cartridge of claim 1, wherein:
   the first set of IOL manipulators comprises a pair of edge rollers pivotably attached to an interior portion of the IOL cartridge; and
   the second set of IOL manipulators comprises a pair of compression arms pivotably attached to an interior portion of the IOL cartridge.

3. The IOL cartridge of claim 1, further comprising a plunger case in fluid communication with the compartment, wherein a plunger is movably disposed within the plunger case.

4. The IOL cartridge of claim 1, wherein the cap comprises a latch that is removably fastened to the actuator.

5. The IOL cartridge of claim 1, further comprising an IOL loaded in the compartment of the housing.

6. A method for delivery of an intraocular lens (IOL) into an eye, comprising:
   attaching an IOL cartridge to a handpiece, the IOL cartridge comprising:
      a housing comprising a compartment having an IOL disposed therein;
      a nozzle coupled to the housing and in fluid communication with the compartment;
      an actuator coupled to the housing and configured to translate along an exterior portion of the housing relative to the compartment from a first position to a second position;
      a first and a second set of internal ramps operably connected to the actuator; and
      a first and a second set of IOL manipulators inside the compartment; and
   translating the actuator from the first position to the second position to move the first and second set of internal ramps to actuate the first and the second set of IOL manipulators, respectively, to fold or straighten the IOL.

7. The method of claim 6, further comprising inserting the nozzle into an eye.

8. The method of claim 7, further comprising actuating the handpiece to deliver the IOL from the compartment through the nozzle and into the eye.

9. The method of claim 8, wherein:
   the IOL cartridge further comprises a plunger case in fluid communication with the compartment;
   the handpiece further comprises a plunger movably disposed within the plunger case when the IOL cartridge is attached to the handpiece; and
   actuating the handpiece comprises actuating a drive mechanism to translate the plunger through the plunger case to deliver the IOL from the compartment.

10. The method of claim 8, further comprising removing the IOL cartridge from the handpiece after delivering the IOL into the eye.

11. The method of claim 6, wherein the IOL cartridge further comprises a cap adapted to at least partially cover at least one of the nozzle, the housing, and the actuator, and wherein translating the actuator from the first position to the second position comprises removing the cap to translate the actuator from the first position to the second position.

12. The method of claim 6, wherein the first set of IOL manipulators comprises a pair of edge rollers pivotably attached to an interior portion of the IOL cartridge.

13. The method of claim 12, wherein translating the actuator from the first position to the second position comprises moving each of the first set of internal ramps, as the actuator is translated, to contact a lower portion of one edge roller of the pair of edge rollers to rotate the one edge roller.

14. The method of claim 6, wherein the second set of IOL manipulators comprises a pair of compression arms pivotably attached to an interior portion of the IOL cartridge.

15. The method of claim 14, wherein translating the actuator from the first position to the second position comprises moving each of the second set of internal ramps, as the actuator is translated, to contact a projection of one compression arm of the pair of compression arms to rotate the one compression arm.

16. An intraocular lens (IOL) cartridge comprising:
   a housing;
   a slide disposed within the housing and comprising a first and a second set of internal manipulators;
   a compartment disposed within the housing and configured to receive an IOL, wherein an interior portion of the slide is exposed to the compartment; and
   a cap at least partially covering the slide, the cap configured to translate the slide to move the first and the second set of internal manipulators to fold or straighten the IOL upon removal of the cap.

17. An intraocular lens (IOL) cartridge comprising:
   a housing comprising a compartment configured to receive an IOL;
   a nozzle coupled to the housing and in fluid communication with the compartment;

an actuator coupled to the housing and configured to translate along an exterior portion of the housing relative to the compartment from a first position to a second position; and a first and a second set of internal ramps operably connected to the actuator, wherein as the actuator is translated from the first position to the second position, the first and the second set of internal ramps are configured to actuate a first and a second set of IOL manipulators, respectively, to manipulate the IOL for delivery, the first set of IOL manipulators comprising a pair of edge rollers pivotably attached to an interior portion of the IOL cartridge.

18. The IOL cartridge of claim 17, wherein each internal ramp of the first set of internal ramps is configured to contact a lower portion of one edge roller of the pair of edge rollers and to rotate the one edge roller upon translation of the actuator from the first position to the second position.

19. An intraocular lens (IOL) cartridge comprising:
a housing comprising a compartment configured to receive an IOL;
a nozzle coupled to the housing and in fluid communication with the compartment;
an actuator coupled to the housing and configured to translate along an exterior portion of the housing relative to the compartment from a first position to a second position; and a first and a second set of internal ramps operably connected to the actuator, wherein as the actuator is translated from the first position to the second position, the first and the second set of internal ramps are configured to actuate a first and a second set of IOL manipulators, respectively, to manipulate the IOL for delivery, the second set of IOL manipulators comprising a pair of compression arms pivotably attached to an interior portion of the IOL cartridge.

20. The IOL cartridge of claim 19, wherein each internal ramp of the second set of internal ramps is configured to contact a projection of one compression arm of the pair of compression arms and to rotate the one compression arm upon translation of the actuator from the first position to the second position.

* * * * *